United States Patent
Hiraguchi et al.

(10) Patent No.: US 11,318,236 B2
(45) Date of Patent: May 3, 2022

(54) OXYGENATOR AND METHOD FOR MANUFACTURING THE SAME

(71) Applicant: TERUMO KABUSHIKI KAISHA, Tokyo (JP)

(72) Inventors: Ryuji Hiraguchi, Elkton, MD (US); Akira Gyoten, Elkton, MD (US)

(73) Assignee: Terumo Kabushiki Kaisha, Tokyo (JP)

( * ) Notice: Subject to any disclaimer, the term of this patent is extended or adjusted under 35 U.S.C. 154(b) by 175 days.

(21) Appl. No.: 16/933,211

(22) Filed: Jul. 20, 2020

(65) Prior Publication Data

US 2020/0345918 A1    Nov. 5, 2020

Related U.S. Application Data

(63) Continuation of application No. PCT/JP2018/003719, filed on Feb. 5, 2018.

(51) Int. Cl.
*B01D 53/22* (2006.01)
*A61M 1/16* (2006.01)
*B01D 19/00* (2006.01)
*B01D 63/02* (2006.01)
(Continued)

(52) U.S. Cl.
CPC ........ *A61M 1/1698* (2013.01); *A61M 1/1629* (2014.02); *B01D 19/0031* (2013.01); *B01D 63/021* (2013.01); *B01D 65/003* (2013.01); *B01D 69/08* (2013.01);
(Continued)

(58) Field of Classification Search
CPC .............. B01D 63/021; B01D 2313/14; B01D 19/0031; B01D 2313/22; B01D 69/08; B01D 65/003; A61M 1/1698; A61M 2207/00
See application file for complete search history.

(56) References Cited

U.S. PATENT DOCUMENTS 5,429,184 A    7/1995 Bach et al.
2018/0207344 A1    7/2018 Hisamatsu et al.

FOREIGN PATENT DOCUMENTS

JP    H04200562 A    7/1992
JP    2001079083 A    3/2001
(Continued)

OTHER PUBLICATIONS

Translation of Written Opinion of the ISA, PCT/JP2018/003719, dated Mar. 27, 2018.
(Continued)

*Primary Examiner* — Anthony R Shumate
(74) *Attorney, Agent, or Firm* — MacMillan, Sobanski & Todd, LLC

(57) ABSTRACT

In a method for manufacturing an oxygenator, an intermediate spacer is disposed between a cylindrical heat exchange unit configured by winding a first hollow fiber membrane and a cylindrical gas exchange unit configured by winding a second hollow fiber membrane so that a first gap is formed between one end portions of the heat exchange unit and the gas exchange unit, and a first partition section of a first cover member is inserted into the first gap. In such an oxygenator, a first end portion of the intermediate spacer is located at a part that does not overlap the first partition section in a radial direction in the heat exchange unit and the gas exchange unit. The intermediate spacer is formed by winding an intermediate hollow fiber membrane.

11 Claims, 15 Drawing Sheets

(51) Int. Cl.
*B01D 65/00* (2006.01)
*B01D 69/08* (2006.01)

(52) U.S. Cl.
CPC ..... *A61M 2207/00* (2013.01); *B01D 2313/14* (2013.01); *B01D 2313/22* (2013.01)

(56) References Cited

FOREIGN PATENT DOCUMENTS

| | | |
|---|---|---|
| JP | 2016039995 A | 3/2016 |
| WO | 2016009780 A1 | 1/2016 |

OTHER PUBLICATIONS

International Search Report, PCT/JP2018/003719, dated Mar. 27, 2018.

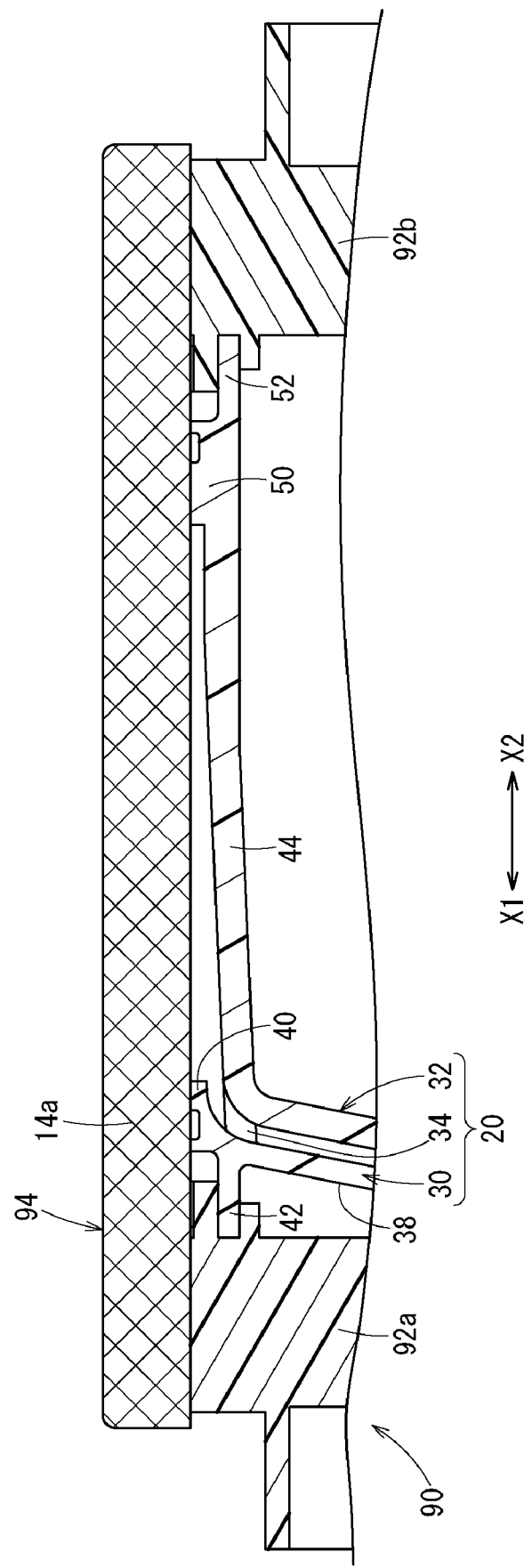

OXYGENATOR AND METHOD FOR MANUFACTURING THE SAME

CROSS REFERENCE TO RELATED APPLICATIONS

This application is a continuation of PCT Application No. PCT/JP2018/003719, filed Feb. 5, 2018, which is incorporated herein by reference in its entirety.

BACKGROUND OF THE INVENTION

The present invention relates to an oxygenator in which a cylindrical heat exchange unit configured by winding a first hollow fiber membrane and a cylindrical gas exchange unit configured by winding a second hollow fiber membrane are accommodated in a housing in a state of being disposed to overlap each other in a radial direction so that a blood flow path is formed on an outer side of the first hollow fiber membrane and an outer side of the second hollow fiber membrane, and a method for manufacturing the same.

This kind of oxygenator is disclosed in, for example, WO2016/009780A. The housing of this oxygenator includes a pair of partition sections which partitions spaces on both sides in the axial direction from the heat exchange unit and the gas exchange unit into a heat medium flow path and a gas flow path.

In the oxygenator described above, a partition section is inserted between the end portions of the heat exchange unit and the gas exchange unit when the housing is assembled in some cases. However, in the conventional oxygenator, the second hollow fiber membrane of the gas exchange unit is wound around the outer surface of the first hollow fiber membrane of the heat exchange unit, and thus the end portion of the heat exchange unit and the end portion of the gas exchange unit are pushed in the radial direction by the partition section. In this case, there is the possibility that the lumen of the first hollow fiber membrane and the lumen of the second hollow fiber membrane are collapsed and the heat exchange rate and the gas exchange rate decrease.

SUMMARY OF THE INVENTION

The present invention has been made in view of such problems, and an object thereof is to provide an oxygenator capable of alleviating decreases in a heat exchange rate and a gas exchange rate even in a case in which each of the heat exchange unit and the gas exchange unit is formed by winding a hollow fiber membrane, and a method for manufacturing the same.

In order to achieve the above object, the oxygenator according to the present invention is an oxygenator in which a cylindrical heat exchange unit configured by winding a first hollow fiber membrane and a cylindrical gas exchange unit configured by winding a second hollow fiber membrane are accommodated in a housing in a state of being disposed to overlap each other in a radial direction so that a blood flow path is formed on an outer side of the first hollow fiber membrane and an outer side of the second hollow fiber membrane, the housing includes a pair of partition sections that partitions each of spaces on both sides in an axial direction from the heat exchange unit and the gas exchange unit into a heat medium flow path and a gas flow path, the partition sections are each inserted between end portions of the heat exchange unit and the gas exchange unit, a cylindrical intermediate spacer is arranged between the heat exchange unit and the gas exchange unit by winding an intermediate hollow fiber membrane, and at least one end portion of the intermediate spacer is located at a part that does not overlap the partition section in the radial direction in the end portions of the heat exchange unit and the gas exchange unit.

According to such a configuration, it is possible to form a gap, into which a protruding end of the partition section can be inserted, between the end portions of the heat exchange unit and the gas exchange unit by the intermediate spacer. Hence, the end portion of the heat exchange unit and the end portion of the gas exchange unit are pushed in the radial direction by the partition section and it is possible to suppress the lumen of the first hollow fiber membrane and the lumen of the second hollow fiber membrane from being collapsed. Consequently, it is possible to avoid decreases in the heat exchange rate and the gas exchange rate. In addition, the intermediate spacer is configured by winding an intermediate hollow fiber membrane, and it is thus possible to easily adjust the thickness of the intermediate spacer itself depending on the thickness of the partition sections of the housing.

In the oxygenator, a thickness of the protruding part of the partition section inserted between the end portions of the heat exchange unit and the gas exchange unit may be thinner than a radial thickness of the intermediate spacer.

According to such a configuration, it is possible to further suppress the lumen of the first hollow fiber membrane and the lumen of the second hollow fiber membrane from being collapsed by the partition section.

In the oxygenator, the intermediate spacer may be formed so that a fluid does not flow through a lumen of the intermediate hollow fiber membrane.

According to such a configuration, it is possible to avoid a decrease in the heat exchange rate or the gas exchange rate due to the gas (oxygen) and heat medium flowing through the lumen of the intermediate hollow fiber membrane.

In the oxygenator, the intermediate spacer may be comprised of one continuous intermediate hollow fiber membrane and an opening at least at one end portion of the intermediate hollow fiber membrane comprising the intermediate spacer may be closed.

According to such a configuration, it is possible to prevent the heat medium or gas from flowing through the lumen of the intermediate hollow fiber membrane of the intermediate spacer.

In the oxygenator, the intermediate spacer may be formed as the intermediate hollow fiber membranes overlap each other in the radial direction.

According to such a configuration, it is possible to easily adjust the thickness (wall thickness) of the intermediate spacer.

In the oxygenator, each protruding end portion of the intermediate spacer may be located at a region that does not overlap the partition section in the radial direction in the end portions of the heat exchange unit and the gas exchange unit.

According to such a configuration, it is possible to form a gap, into which a protruding end of the partition section can be inserted, between the end portions of both the heat exchange unit and the gas exchange unit by the intermediate spacer. Consequently, it is possible to further avoid decreases in the heat exchange rate and the gas exchange rate.

The method for manufacturing an oxygenator according to the present invention is a method for manufacturing an oxygenator including a heat exchange unit and a gas exchange unit that are disposed to overlap each other in a radial direction, the method sequentially performing: a first winding step of forming a first cylindrical unit by winding a first hollow fiber membrane on an outer surface of a core; an arrangement step of arranging a cylindrical intermediate spacer by winding an intermediate hollow fiber membrane around an outer surface of the first cylindrical unit; a second winding step of forming a second cylindrical unit by winding a second hollow fiber membrane around an outer surface of the intermediate spacer; an outer cylinder disposition step of disposing an outer cylinder so as to cover an outer surface of the second cylindrical unit; a cutting step of forming the heat exchange unit and the gas exchange unit by cutting both end portions of the first cylindrical unit and the second cylindrical unit; a sealing step of sealing outer sides of the first hollow fiber membrane and the second hollow fiber membrane at both end portions of the heat exchange unit and the gas exchange unit with a sealing member; and a mounting step of mounting cover members on both end portions of the core and the outer cylinder and forming a heat medium flow path and a gas flow path in the respective cover members, in which the intermediate spacer is arranged on the outer surface of the first cylindrical unit so that a gap is formed at least between one end portions of the heat exchange unit and the gas exchange unit or between the other end portions of the heat exchange unit and the gas exchange unit when performing the mounting step in the arrangement step, and a partition section of the cover member is inserted into the gap formed by the intermediate spacer in the mounting step.

According to such a method, it is possible to manufacture the oxygenator described above.

In the method for manufacturing an oxygenator, the intermediate spacer may be arranged on the outer surface of the first cylindrical unit so that the gap is formed between one end portions of the heat exchange unit and the gas exchange unit and between the other end portions of the heat exchange unit and the gas exchange unit when performing the mounting step in the arrangement step and the partition section of each of the cover members may be inserted into each of the gaps formed by the intermediate spacer in the mounting step.

According to such a method, it is possible to further avoid decreases in the heat exchange rate and the gas exchange rate.

In the method for manufacturing an oxygenator, an annular member may be disposed so as to cover only both end portions of the first cylindrical unit in the arrangement step, the second hollow fiber membrane may be wound around an outer surface of each of the intermediate spacer and the annular member in the second winding step, and a removal step of removing the annular member may be performed after the sealing step.

According to such a method, it is possible to reliably form a gap, into which the partition section can be inserted, between the end portions of both the heat exchange unit and the gas exchange unit by the annular member.

In the method for manufacturing an oxygenator, the first cylindrical unit may be formed by winding one continuous first hollow fiber membrane around the outer surface of the first cylindrical unit and reciprocating the one continuous first hollow fiber membrane a plurality of times in an axial direction in the first winding step and the second cylindrical unit may be formed by winding one continuous second hollow fiber membrane around the outer surface of the intermediate spacer and reciprocating the one continuous second hollow fiber membrane a plurality of times in the axial direction in the second winding step.

According to such a method, it is possible to efficiently form the first cylindrical unit and the second cylindrical unit.

In the method for manufacturing an oxygenator, an opening at least at one end portion of the intermediate hollow fiber membrane constituting the intermediate spacer may be closed with the sealing member in the sealing step.

According to such a method, it is possible to prevent the fluid from flowing through the lumen of the intermediate hollow fiber.

According to the present invention, it is possible to form a gap, into which a partition section can be inserted, between end portions of a heat exchange unit and a gas exchange unit by an intermediate spacer and thus to prevent a lumen of a first hollow fiber membrane and a lumen of a second hollow fiber membrane from being collapsed by the partition section. Consequently, it is possible to suppress decreases in the heat exchange rate and the gas exchange rate.

BRIEF DESCRIPTION OF THE DRAWINGS

FIG. 7 is a partial longitudinal sectional explanatory view of FIG. 6B;

DETAILED DESCRIPTION OF PREFERRED EMBODIMENTS

Hereinafter, suitable embodiments of the oxygenator according to the present invention will be described with reference to the attached drawings in relation to a method for manufacturing the same.

Figure 1:
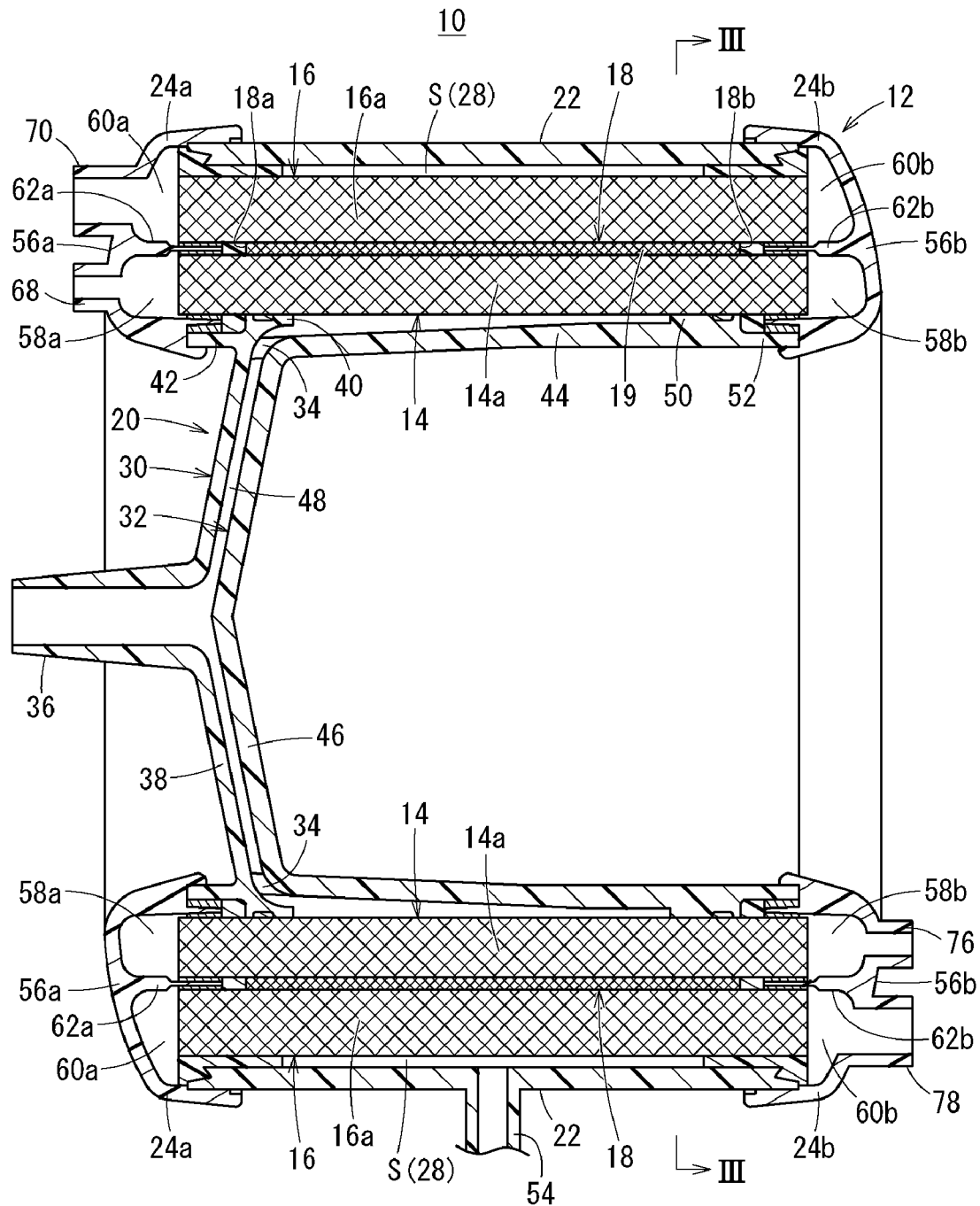
FIG. 1 is a longitudinal sectional view of an oxygenator according to an embodiment of the present invention.

As illustrated in FIG. 1, an oxygenator 10 according to an embodiment of the present invention is a medical instrument that temporarily substitutes for the function of lung in the operation of heart surgery and the like of a human body. Specifically, the oxygenator 10 is a device for adjusting the blood temperature, removing carbon dioxide in blood, and supplying oxygen to blood in extracorporeal blood circulation.

Figure 2:
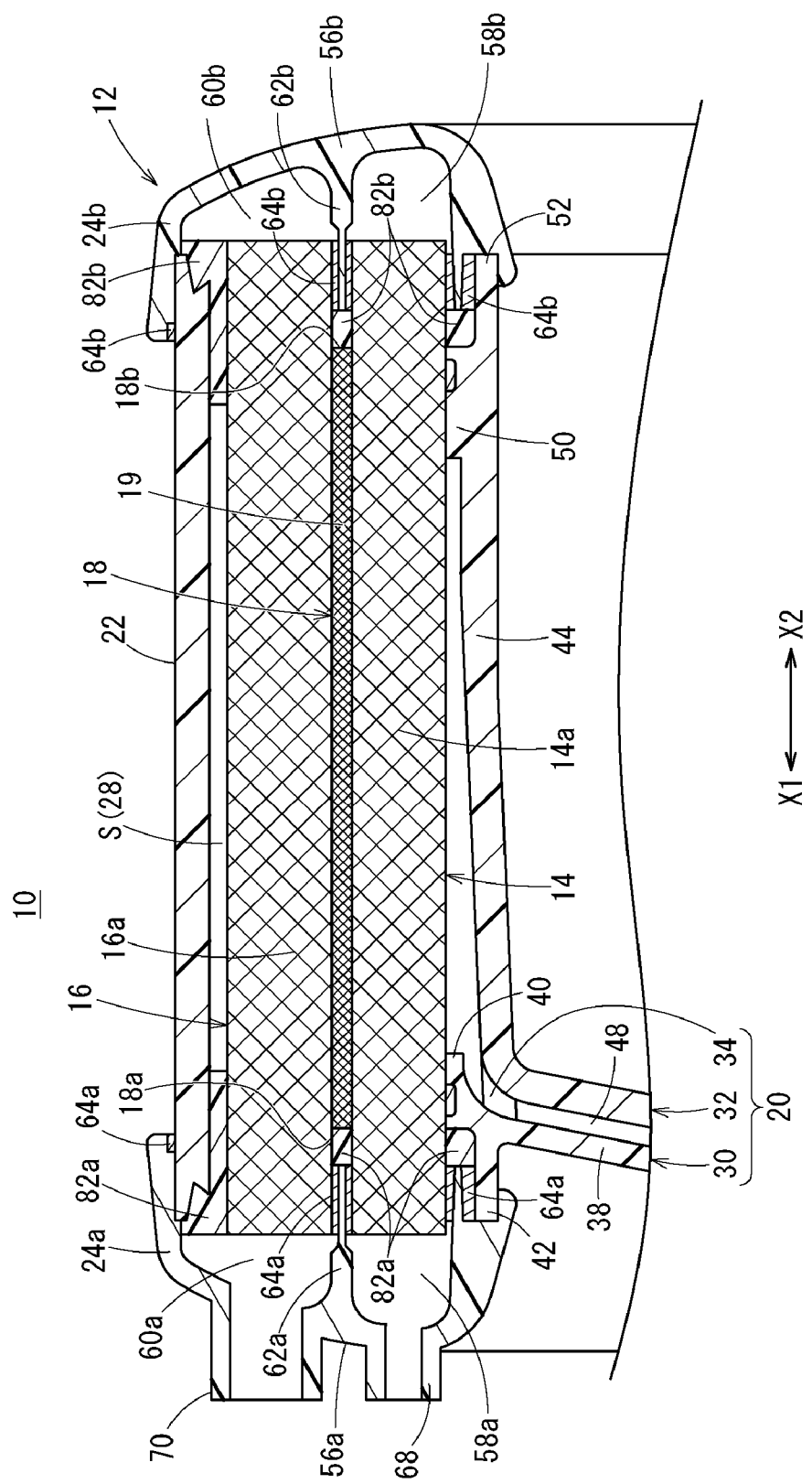
FIG. 2 is a partially enlarged sectional view of the oxygenator illustrated in FIG. 1.
Figure 3:
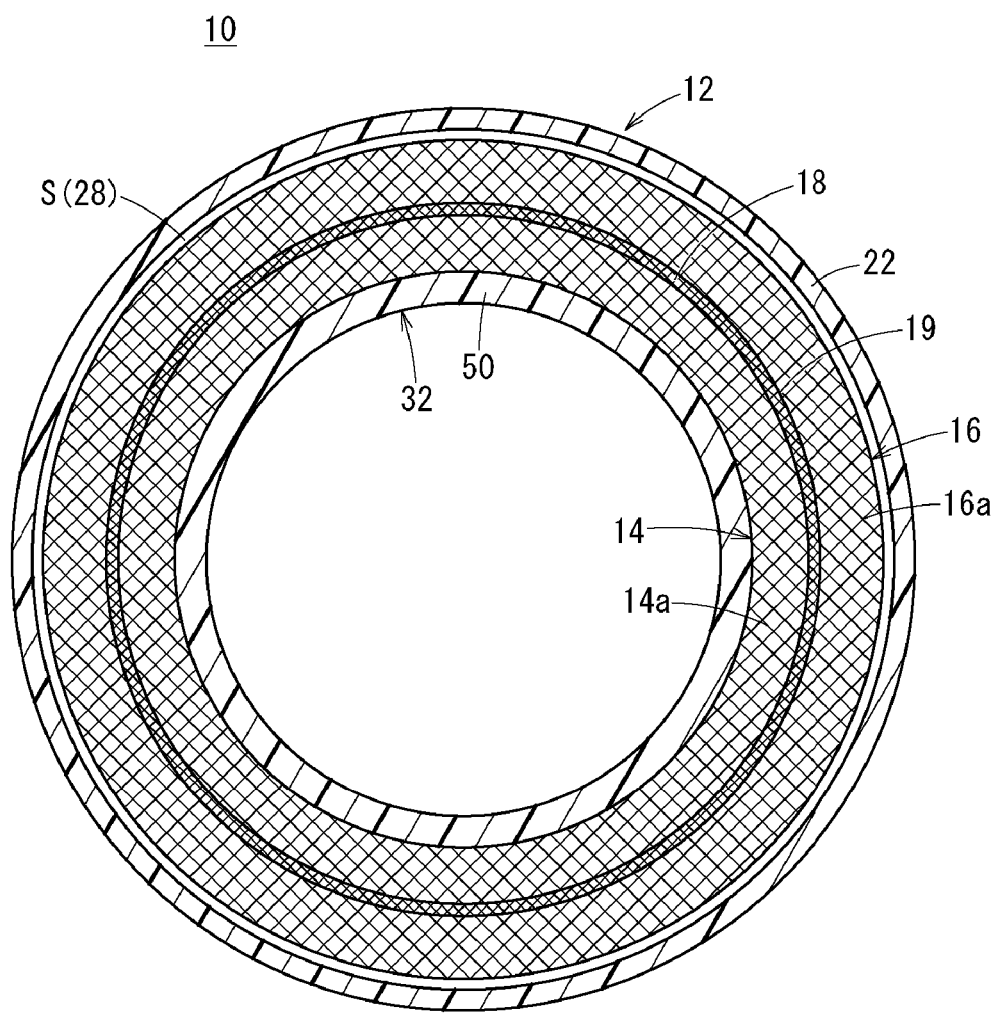
FIG. 3 is a transverse sectional view taken along the line III-III in FIG. 1.

As illustrated in FIGS. 1 to 3, the oxygenator 10 includes a housing 12, a heat exchange unit 14, a gas exchange unit 16, and an intermediate spacer 18.

In FIG. 1, the housing 12 includes a core 20 constituting a central part of the oxygenator 10, an outer cylinder 22 provided on an outer peripheral side of the core 20, a first cover member 24a mounted on one end portion of the core 20 and one end portion of the outer cylinder 22, and a second cover member 24b mounted on the other end portion of the core 20 and the other end portion of the outer cylinder 22.

The core 20, the outer cylinder 22, the first cover member 24a, and the second cover member 24b form an annular accommodation space S for accommodating the cylindrical heat exchange unit 14 and the cylindrical gas exchange unit 16. The accommodation space S functions as a blood flow path 28. Each of the core 20, the outer cylinder 22, the first cover member 24a, and the second cover member 24b is integrally formed of a hard resin.

The core 20 includes a first core section 30 constituting one end portion of the core 20 and a second core section 32 constituting a part including the other end portion of the core 20. The first core section 30 and the second core section 32 are connected to each other by a plurality of connection portions 34.

The first core section 30 has a blood inflow portion 36 to which a tube (not illustrated) can be connected at one end portion and an annular wall portion 38 extending radially outward from the blood inflow portion 36. The outer end portion of the wall portion 38 is provided with a first support portion 40 for supporting the heat exchange unit 14 and a first annular convex portion 42 protruding from the first support portion 40 to one side (the arrow X1 direction in FIG. 1) of the outer cylinder 22 in the axial direction.

The second core section 32 is formed in a bottomed cylindrical shape and has a cylinder portion 44 and a closing portion 46 provided at one end portion (the end portion in the arrow X1 direction) of the cylinder portion 44. The closing portion 46 is disposed so as to face the wall portion 38 with a gap. The gap between the closing portion 46 and the wall portion 38 functions as a blood introduction path 48 for guiding the blood flowing from the blood inflow portion 36 into the accommodation space S. The outer surface of the cylinder portion 44 is provided with a second support portion 50 for supporting the heat exchange unit 14 and a second annular convex portion 52 protruding from the second support portion 50 to the other end side (the arrow X2 direction in FIG. 1) of the outer cylinder 22 in the axial direction. The second support portion 50 is located at the other end portion of the cylinder portion 44.

The outer cylinder 22 is a cylindrical member disposed radially outward from the core 20 with a gap (see FIG. 3). The entire length of the outer cylinder 22 in the axial direction is slightly longer than the entire length of the second core section 32 in the axial direction. The outer cylinder 22 is provided with a blood outflow portion 54 for allowing blood in the accommodation space S to flow out.

As illustrated in FIGS. 1 and 2, the first cover member 24a has a first cover main body 56a provided so as to face one end surface of the heat exchange unit 14 and one end surface of the gas exchange unit 16 with a gap and a first partition section 62a which partitions a space in the first cover main body 56a into a first heat medium flow path 58a and a first gas flow path 60a.

The first cover main body 56a extends in an annular shape and in the axial direction. The inner end portion (radially inner end portion) of the first cover main body 56a is fixed to the first annular convex portion 42 with an adhesive 64a. The outer end portion (radially outer end portion) of the first cover main body 56a is fixed to the outer cylinder 22 with the adhesive 64a. The first cover main body 56a is provided with a heat medium inflow portion 68 for allowing a heat medium to flow into the first heat medium flow path 58a and a gas inflow portion 70 for allowing a gas (oxygen gas) to flow into the first gas flow path 60a.

The first partition section 62a protrudes in the axial direction from the inner surface of the first cover main body 56a toward the side on which the heat exchange unit 14 and the gas exchange unit 16 are located and extends annularly. The protruding end portion of the first partition section 62a is fixed with the adhesive 64a in the state of being inserted between one end portions of the heat exchange unit 14 and the gas exchange unit 16. The thickness of the protruding end portion of the first partition section 62a (the part inserted between one end portions of the heat exchange unit 14 and the gas exchange unit 16 of the first partition section 62a) is thinner than the wall thickness of the intermediate spacer 18. The thickness of the root portion of the first partition section 62a (the part near the first cover main body 56a) is thicker than the thickness of the protruding end portion of the first partition section 62a.

The first heat medium flow path 58a is a flow path for guiding the heat medium to the heat exchange unit 14 and is located radially inward from the first partition section 62a. The first gas flow path 60a is a path for guiding the oxygen gas to the gas exchange unit 16 and is located radially outward from the first partition section 62a.

The second cover member 24b has a second cover main body 56b provided so as to face the other end surface of the heat exchange unit 14 and the other end surface of the gas exchange unit 16 with a gap and a second partition section 62b which partitions a space in the second cover main body 56b into a second heat medium flow path 58b and a second gas flow path 60b.

The second cover main body 56b extends annularly. The inner end portion of the second cover main body 56b is fixed to the second annular convex portion 52 with an adhesive 64b. The outer end portion of the second cover main body 56b is fixed to the outer cylinder 22 with the adhesive 64b. In FIG. 1, the second cover main body 56b is provided with a heat medium outflow portion 76 for allowing the heat medium in the second heat medium flow path 58b to flow out and a gas outflow portion 78 for allowing the gas (carbon dioxide gas) in the second gas flow path 60b to flow out to the outside.

As illustrated in FIGS. 1 and 2, the second partition section 62b protrudes from the inner surface of the second cover main body 56b toward the side on which the heat exchange unit 14 and the gas exchange unit 16 are located and extends in an annular shape. The protruding end portion of the second partition section 62b is liquid-tightly and air-tightly fixed with the adhesive 64b in the state of being inserted between the other end portions of the heat exchange unit 14 and the gas exchange unit 16. The thickness of the protruding end portion of the second partition section 62b (the part inserted between the other end portions of the heat exchange unit 14 and the gas exchange unit 16 of the second partition section 62b) is thinner than the wall thickness of the intermediate spacer 18. The thickness of the root portion of the second partition section 62b (the part near the second cover main body 56b) is thicker than the thickness of the protruding end portion of the second partition section 62b.

The second heat medium flow path 58b is a flow path for guiding the heat medium guided from the heat exchange unit 14 to the heat medium outflow portion 76 and is located radially inward from the second partition section 62b. The second gas flow path 60b is a flow path for guiding the gas (carbon dioxide gas) guided from the gas exchange unit 16 to the gas outflow portion 78 and is located radially outward from the second partition section 62b.

The heat exchange unit 14 is for performing heat exchange between the blood flowing in the blood flow path 28 and the heat medium. As the heat medium, for example, water (pure water) is used. However, the heat medium is not limited to water and may be another liquid or a gas. The entire length of the heat exchange unit 14 is slightly longer than the entire length of the outer cylinder 22. In other words, both end portions of the heat exchange unit 14 protrude to the outer side of the outer cylinder 22.

The heat exchange unit 14 is formed in a cylindrical shape by a plurality of first hollow fiber membranes 14a. Each first hollow fiber membrane 14a is wound around the outer surface of the core 20 (the first support portion 40 and the second support portion 50) so as to extend over the entire length of the heat exchange unit 14. A gap through which blood can flow is formed between the first hollow fiber membranes 14a adjacent to each other. The opening at one end of each first hollow fiber membrane 14a communicates with the interior of the first heat medium flow path 58a, and the opening at the other end of each first hollow fiber membrane 14a communicates with the interior of the second heat medium flow path 58b. In other words, the heat medium flows through the lumen of each first hollow fiber membrane 14a.

The first hollow fiber membrane 14a is configured so as not to allow the heat medium and blood to pass therethrough. As a constituent material for the first hollow fiber membrane 14a, for example, polymer materials such as polypropylene, polyamide, polyethylene, polysulfone, polyacrylonitrile, polytetrafluoroethylene, and polymethylpentene are used and polyamide is preferable. The inner diameter of the first hollow fiber membrane 14a is preferably set to, for example, a range of 50 μm to 700 μm. In this case, the flow resistance of the heat medium flowing through the lumen of the first hollow fiber membrane 14a can be decreased to a relatively low value. The outer diameter of the first hollow fiber membrane 14a is preferably set to a range of 100 μm to 1000 μm, and more preferably to a range of 120 μm to 800 μm. In this case, the surface area of the first hollow fiber membrane 14a can be efficiently increased.

The gas exchange unit 16 is for supplying oxygen gas to the blood flowing through the blood flow path 28 and removing carbon dioxide in the blood. The gas exchange unit 16 is provided on the outer peripheral side of the heat exchange unit 14. In other words, the gas exchange unit 16 and the heat exchange unit 14 are disposed so as to overlap each other in the radial direction. The entire length of the gas exchange unit 16 is the same as the entire length of the heat exchange unit 14.

The gas exchange unit 16 is formed in a cylindrical shape by a plurality of second hollow fiber membranes 16a. Each second hollow fiber membrane 16a is wound around the outer surface of the intermediate spacer 18 arranged on the outer surface of the heat exchange unit 14 so as to extend over the entire length of the gas exchange unit 16. A gap through which blood can flow is formed between the second hollow fiber membranes 16a adjacent to each other. Then opening at one end of each second hollow fiber membrane 16a communicates with the interior of the first gas flow path 60a, and the opening at the other end of each second hollow fiber membrane 16a communicates with the interior of the second gas flow path 60b. In other words, gas (oxygen gas and carbon dioxide gas) flows through the lumen of each second hollow fiber membrane 16a.

The second hollow fiber membrane 16a is configured so as to allow oxygen gas and carbon dioxide gas to pass therethrough while not allowing blood to pass therethrough. The constituent material for and inner diameter of the second hollow fiber membrane 16a can be set in the same manner as the constituent material for and inner diameter of the first hollow fiber membrane 14a.

As illustrated in FIGS. 1 to 3, the intermediate spacer 18 is arranged on the outer peripheral surface of the heat exchange unit 14. In other words, the intermediate spacer 18 is provided between the heat exchange unit 14 and the gas exchange unit 16. The intermediate spacer 18 is formed in a cylindrical shape and has a first end portion 18a and a second end portion 18b.

In FIGS. 1 and 2, the first end portion 18a (one end portion) of the intermediate spacer 18 is located at the part which does not overlap the first partition section 62a in the radial direction in one end portions of the heat exchange unit 14 and the gas exchange unit 16. In other words, the first end portion 18a of the intermediate spacer 18 is located near the protruding end of the first partition section 62a. In other words, the first end portion 18a of the intermediate spacer 18 is located by being slightly shifted (in the axial direction) on the second cover member 24b side from the protruding end of the first partition section 62a.

The second end portion 18b (the other end portion) of the intermediate spacer 18 is located at the part which does not overlap the second partition section 62b in the radial direction in the other end portions of the heat exchange unit 14 and the gas exchange unit 16. In other words, the second end portion 18b of the intermediate spacer 18 is located near the protruding end of the second partition section 62b. In other words, the second end portion 18b of the intermediate spacer 18 is located by being slightly shifted (in the axial direction) on the first cover member 24a side from the protruding end of the second partition section 62b.

The intermediate spacer 18 is formed in a cylindrical shape by winding one continuous intermediate hollow fiber membrane 19 around the outer peripheral surface of the gas exchange unit 16. The intermediate spacer 18 is formed as the intermediate hollow fiber membranes 19 overlap in the radial direction of the gas exchange unit 16 in a double layer or more. The number of layers of the intermediate hollow fiber membrane 19 is set so that the radial thickness (wall thickness) of the intermediate spacer 18 is thicker than the thickness of the protruding end portion of each of the first partition section 62a and the second partition section 62b. However, the intermediate hollow fiber membranes 19 may not overlap each other in the radial direction of the gas exchange unit 16. In other words, the intermediate hollow fiber membrane 19 may be wound around the outer peripheral surface of the gas exchange unit 16 in a single layer.

As the intermediate hollow fiber membrane 19, the same one as the first hollow fiber membrane 14a is used. However, the inner diameter of and constituent material for the intermediate hollow fiber membrane 19 may be different from the inner diameter of and constituent material for the first hollow fiber membrane 14a. In this case, the inner diameter of and constituent material for the intermediate hollow fiber membrane 19 can be selected from the inner diameters of and constituent materials for the first hollow fiber membrane 14a described above.

As illustrated in FIG. 2, one end side of the accommodation space S is filled with a first sealing member 82a for preventing leakage of blood to the outside (e.g., into the first heat medium flow path 58a and the first gas flow path 60a). Specifically, the first sealing member 82a is added between one end portion of the heat exchange unit 14 and the first annular convex portion 42, between one end portion of the heat exchange unit 14 and one end portion of the gas exchange unit 16, and between one end portion of the gas exchange unit 16 and one end portion of the outer cylinder 22.

The other end side of the accommodation space S is filled with a second sealing member 82b for preventing leakage of blood to the outside (e.g., into the second heat medium flow path 58b and the second gas flow path 60b). Specifically, the second sealing member 82b is added between the other end portion of the heat exchange unit 14 and the second annular convex portion 52, between the other end portion of the heat exchange unit 14 and the other end portion of the gas exchange unit 16, and between the other end portion of the gas exchange unit 16 and the other end portion of the outer cylinder 22. For example, a resin such as urethane is used in each of the first sealing member 82a and the second sealing member 82b.

Next, the operation of the oxygenator 10 configured as described above will be described.

Figure 4:
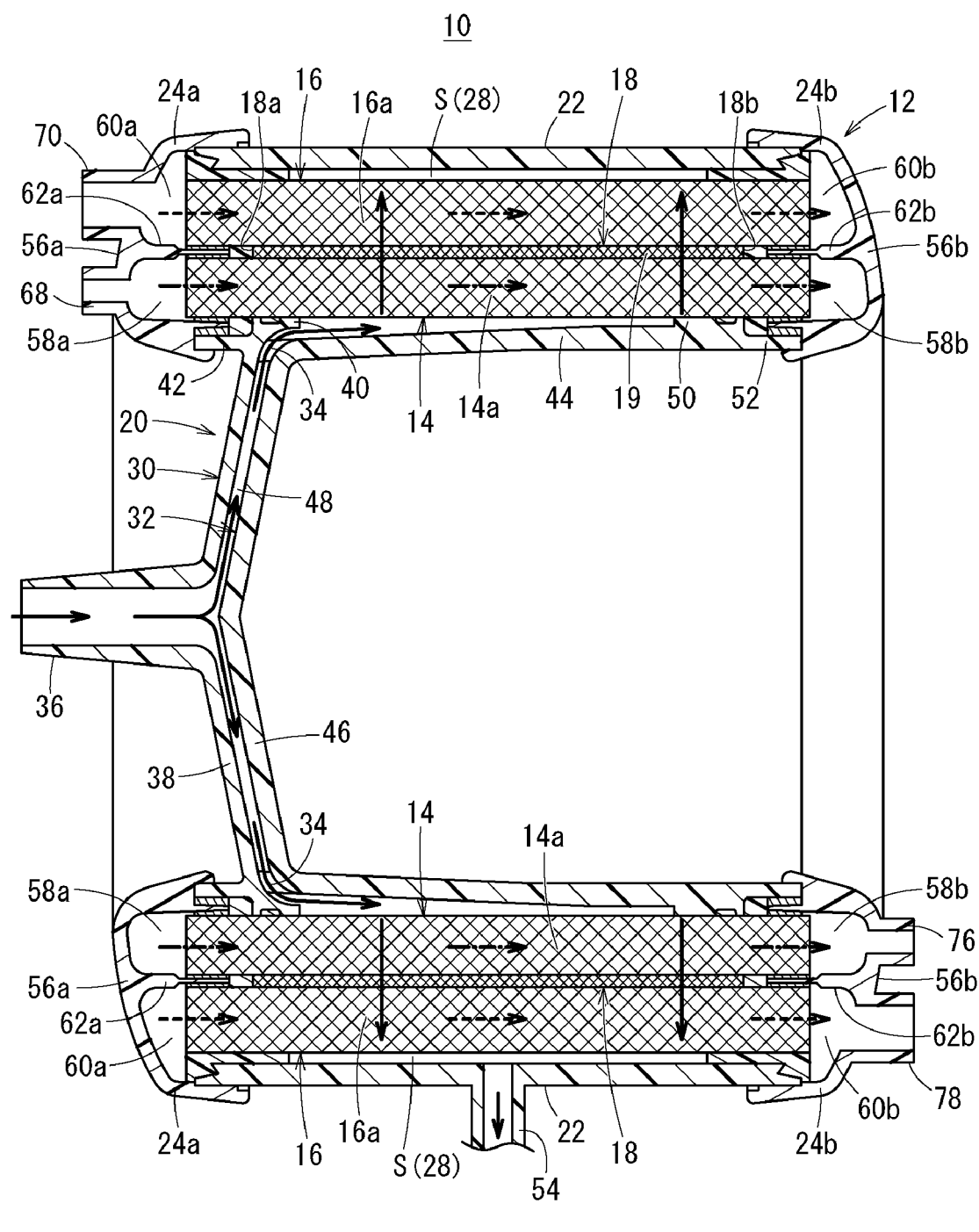
FIG. 4 is an explanatory sectional view illustrating flow of a fluid in an oxygenator.

As illustrated in FIG. 4, in the oxygenator 10, the heat medium is supplied to the heat medium inflow portion 68, oxygen gas is supplied to the gas inflow portion 70, and blood of a human body is guided to the blood inflow portion 36 by a centrifugal pump (not illustrated). The heat medium is introduced from the heat medium inflow portion 68 into the lumen of each first hollow fiber membrane 14a of the heat exchange unit 14 via the first heat medium flow path 58a. Oxygen gas is introduced from the gas inflow portion 70 into the lumen of each second hollow fiber membrane 16a of the gas exchange unit 16 via the first gas flow path 60a.

Blood is guided from the blood inflow portion 36 to the blood flow path 28 (the accommodation space S) via the blood introduction path 48. The blood in the blood flow path 28 flows through the gap between the adjacent first hollow fiber membranes 14a of the heat exchange unit 14 radially outward in the accommodation space S. In this manner, heat exchange between the blood and the heat medium in the first hollow fiber membrane 14a is performed.

The blood subjected to the heat exchange flows through the gap between the adjacent second hollow fiber membranes 16a of the gas exchange unit 16 radially outward in the accommodation space S. In this manner, the oxygen gas in the second hollow fiber membrane 16a passes through the wall portion of the second hollow fiber membrane 16a and is supplied to the blood and the carbon dioxide gas in the blood passes through the wall portion of the second hollow fiber membrane 16a and is removed into the second hollow fiber membrane 16a. The blood subjected to the gas exchange flows in the blood flow path 28 in the circumferential direction, flows out from the blood outflow portion 54 to the outside of the oxygenator 10, and is returned to the human body.

The heat medium subjected to the heat exchange with the blood flows out from the lumen of each first hollow fiber membrane 14a to the outside via the second heat medium flow path 58b and the heat medium outflow portion 76. The carbon dioxide gas in the lumen of each second hollow fiber membrane 16a flows to the outside via the second gas flow path 60b and the gas outflow portion 78.

Next, a method for manufacturing the oxygenator 10 will be described.

Figure 5:
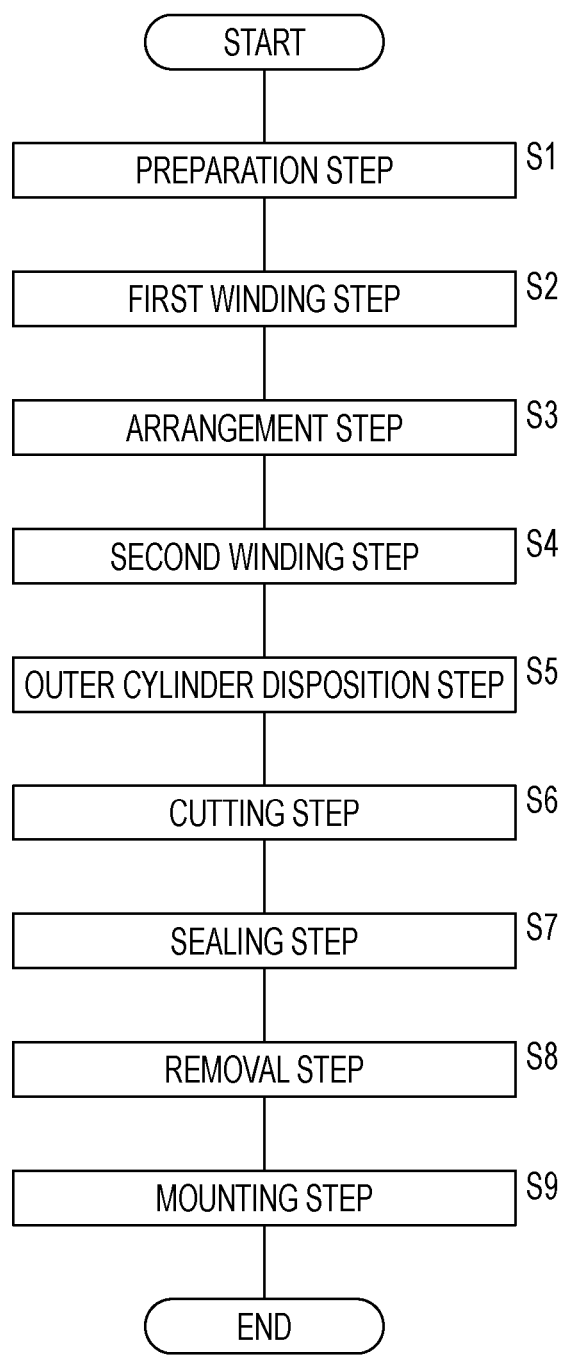
FIG. 5 is a flowchart for explanation of a method for manufacturing the oxygenator illustrated in FIG. 1.
Figure 6A:
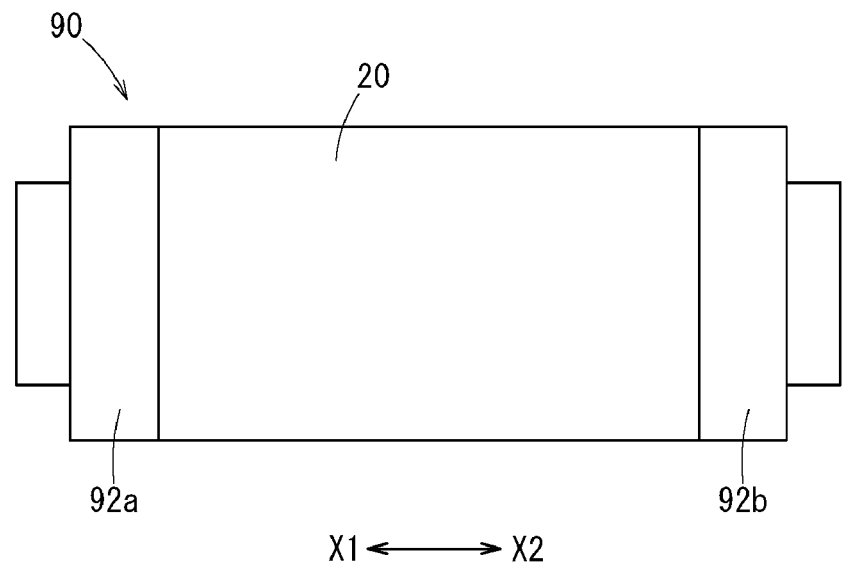
FIG. 6A is an explanatory view of a preparation step.

In the case of manufacturing the oxygenator 10, the preparation step (step S1) in FIG. 5 is performed. In the preparation step, a core member 90 is prepared as illustrated in FIG. 6A. The core member 90 includes the core 20 described above, an annular first cap member 92a mounted on one end of the core 20, and an annular second cap member 92b mounted on the other end of the core 20. The first cap member 92a is fitted to the first annular convex portion 42, and the second cap member 92b is fitted to the second annular convex portion 52 (see FIG. 7).

Figure 6B:
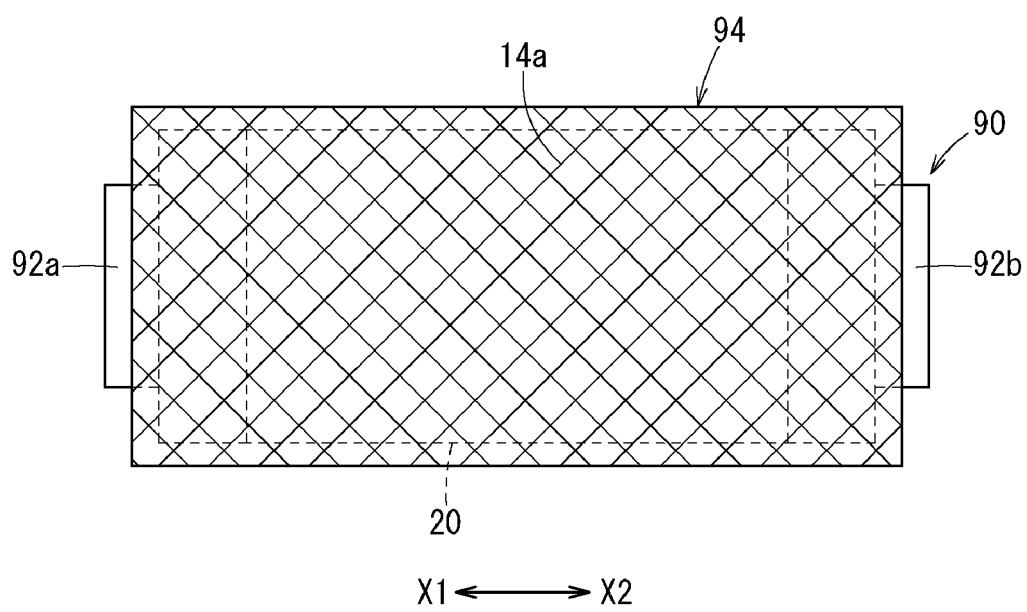
FIG. 6B is an explanatory view of a first winding step.

Subsequently, as illustrated in FIGS. 5, 6B, and 7, a first cylindrical unit 94 is formed by winding the first hollow fiber membrane 14a around the outer peripheral surface of the core member 90 in the first winding step (step S2). Specifically, the first cylindrical unit 94 is formed by circumferentially winding one continuous first hollow fiber membrane 14a around the outer peripheral surface of the core member 90 and reciprocating the first hollow fiber membrane 14a plural times in the axial direction. At this time, the first hollow fiber membrane 14a is also wound around the outer peripheral surfaces of the first cap member 92a and the second cap member 92b.

Figure 8:
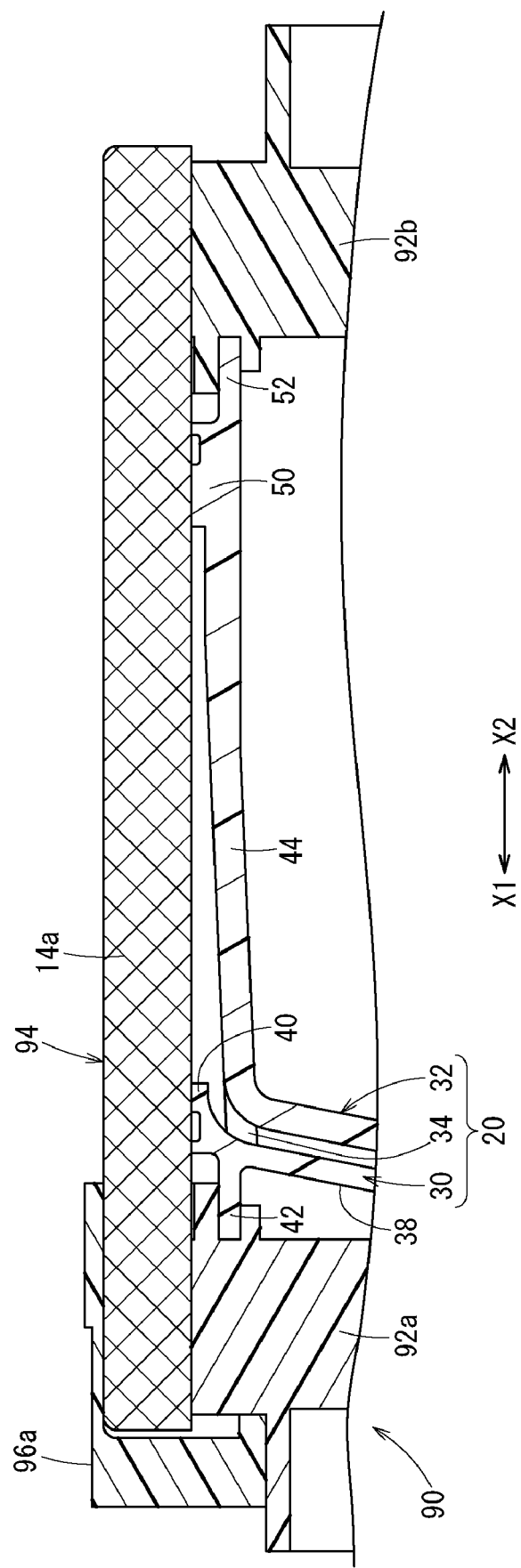
FIG. 8 is a first explanatory view of an arrangement step.
Figure 9:
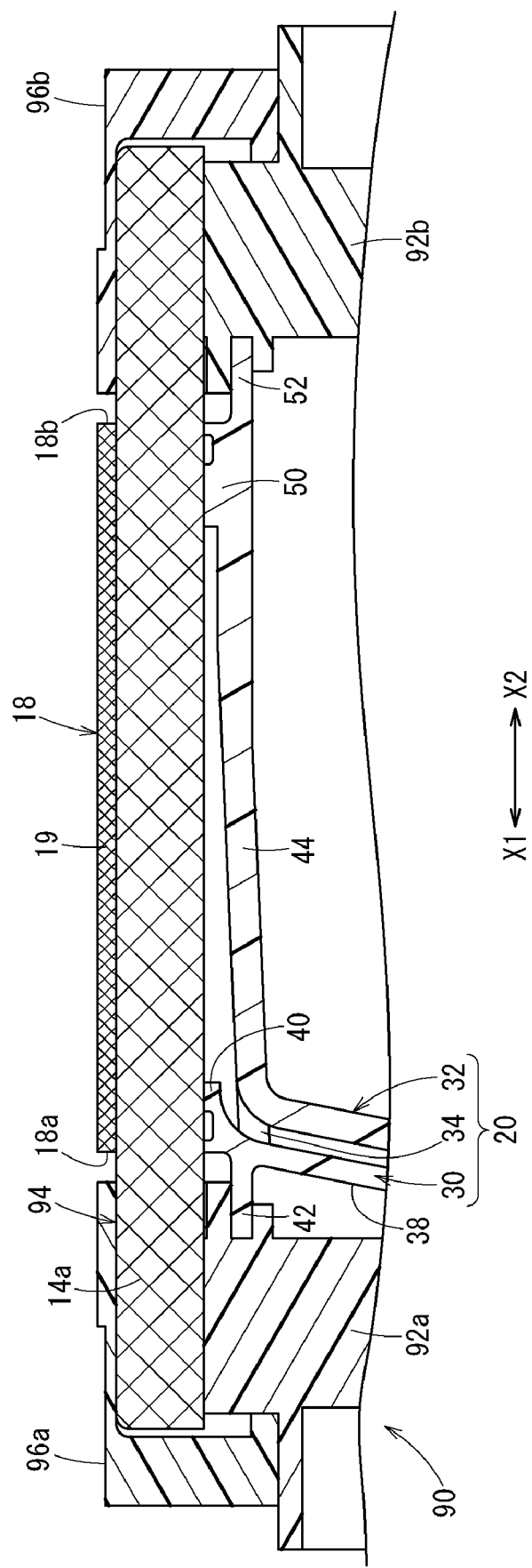
FIG. 9 is a second explanatory view of an arrangement step.

Next, the arrangement step (step S3) in FIG. 5 is performed. In the arrangement step, the first annular member 96a is disposed so as to cover only one end portion of the outer peripheral surface of the first cylindrical unit 94 as illustrated in FIG. 8. The first annular member 96a is mounted on the first cap member 92a. Moreover, the intermediate spacer 18 is arranged at the central part of the outer peripheral surface of the first cylindrical unit 94 as illustrated in FIG. 9. At this time, the intermediate spacer 18 is disposed so that the first end portion 18a is located radially outward from the first support portion 40 and the second end portion 18b is located radially outward from the second support portion 50.

The intermediate spacer 18 is formed by winding the intermediate hollow fiber membrane 19 around the outer peripheral surface of the first cylindrical unit 94. Specifically, the intermediate spacer 18 is formed by circumferentially winding one continuous intermediate hollow fiber membrane 19 around the outer surface of the first cylindrical unit 94 and reciprocating the intermediate hollow fiber membrane 19 plural times in the axial direction.

Figure 10:
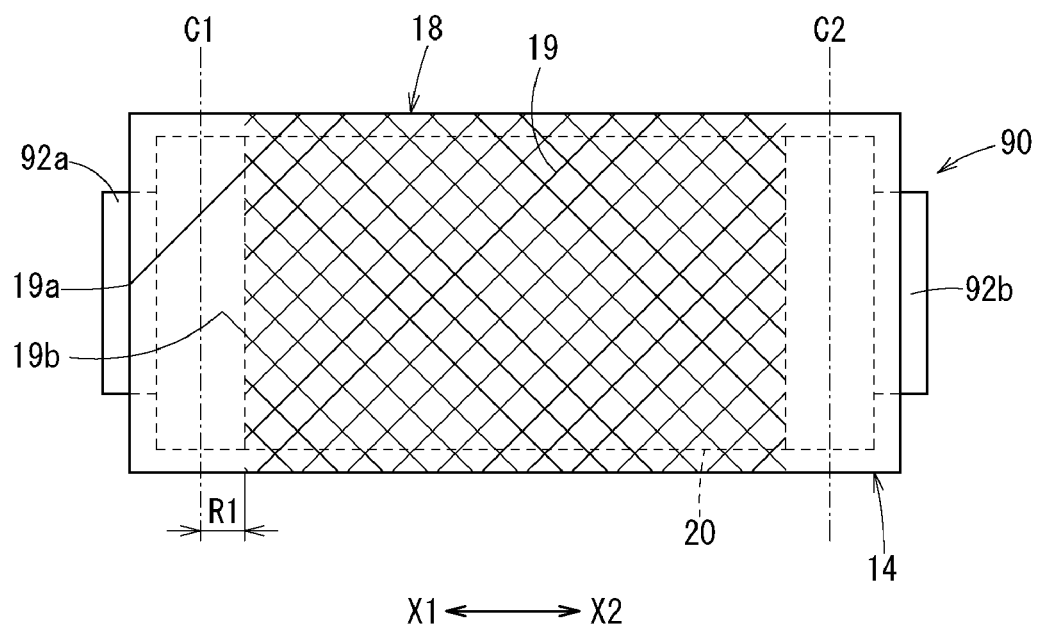
FIG. 10 is an explanatory view illustrating a method for forming an intermediate spacer.

The intermediate hollow fiber membrane 19 and the first hollow fiber membrane 14a are configured as one hollow fiber membrane. Hence, a starting end 19a of the intermediate hollow fiber membrane 19 (the boundary between the intermediate hollow fiber membrane 19 and the first hollow fiber membrane 14a) is located at one end portion of the first cylindrical unit 94. The winding range of the intermediate hollow fiber membrane 19 is shorter than the entire length of the first cylindrical unit 94 (the winding range of the first hollow fiber membrane 14a). In FIG. 10, the intermediate hollow fiber membrane 19 is cut so that a terminal end 19b thereof is located in a range R1 in which the first sealing member 82a is added of the first cylindrical unit 94. In other words, the terminal end 19b of the intermediate hollow fiber membrane 19 is located on the inner side (the second cap member 92b side) of a first cutting line C1 to be cut in the cutting step to be described later. Moreover, the terminal end 19b of the intermediate hollow fiber membrane 19 is temporarily fixed to the first cylindrical unit 94. At this time point, the terminal end 19b of the intermediate hollow fiber membrane 19 is open.

After that, a second annular member 96b is disposed so as to cover only the other end portion of the outer peripheral surface of the first cylindrical unit 94. The second annular member 96b is mounted on the second cap member 92b. In this manner, the intermediate spacer 18 is located between the first annular member 96a and the second annular member 96b.

Figure 11:
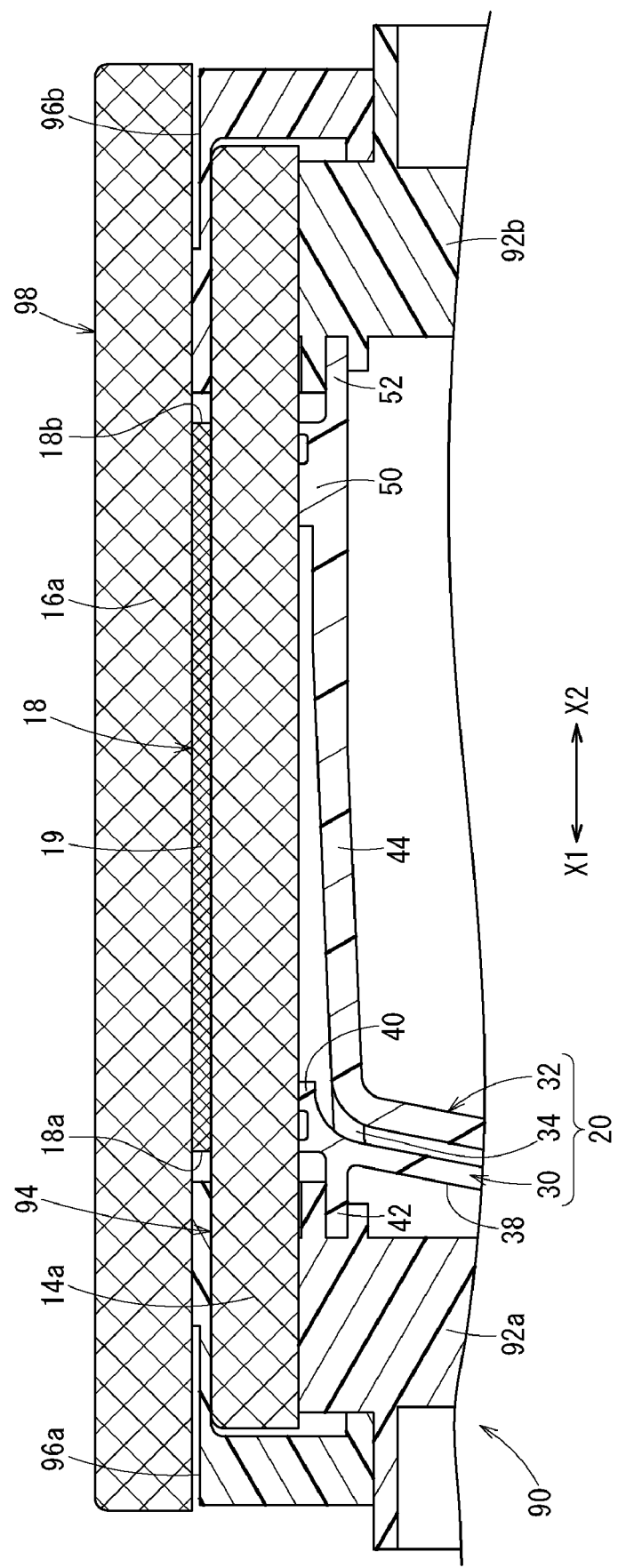
FIG. 11 is an explanatory view of a second winding step.

Subsequently, as illustrated in FIGS. 5 and 11, a second cylindrical unit 98 is formed by winding the second hollow fiber membrane 16a around the outer peripheral surfaces of the first annular member 96a, the intermediate spacer 18, and the second annular member 96b in the second winding step (step S4). Specifically, the second cylindrical unit 98 is formed by continuously winding one continuous second hollow fiber membrane 16a circumferentially around the outer peripheral surfaces of the first annular member 96a, the intermediate spacer 18, and the second annular member 96b and reciprocating the second hollow fiber membrane 16a plural times in the axial direction.

Figure 12:
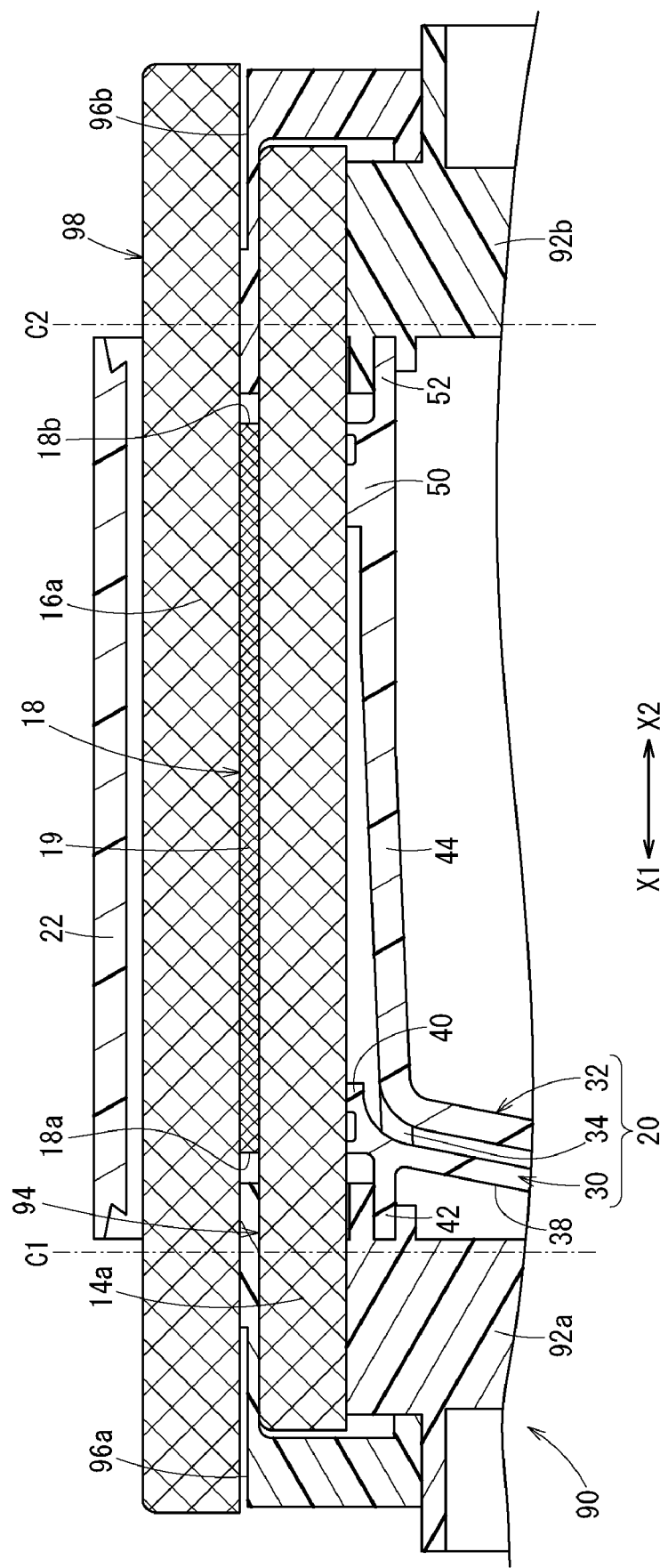
FIG. 12 is an explanatory view of an outer cylinder disposition step.
Figure 13:
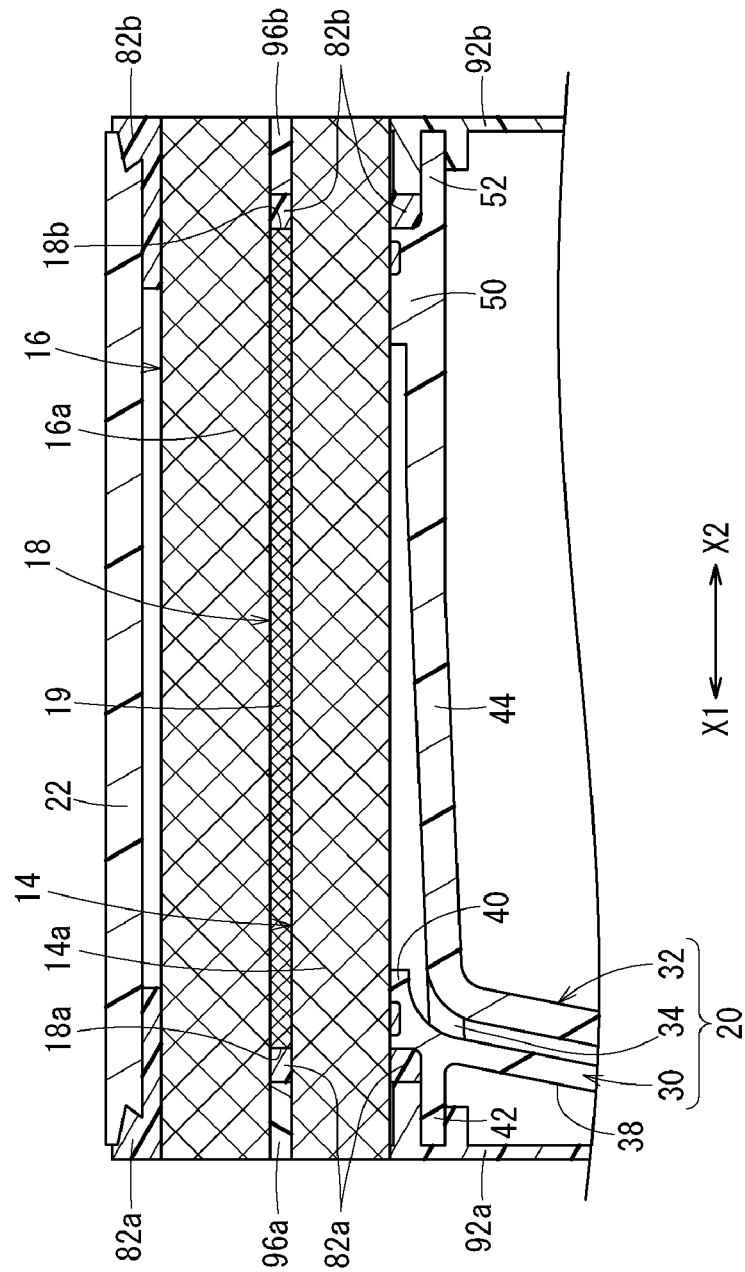
FIG. 13 is an explanatory view of a cutting step and a sealing step.

Next, as illustrated in FIGS. 5 and 12, the outer cylinder 22 is installed so as to cover the outer surface of the second cylindrical unit 98 in the outer cylinder disposition step (step S5). Moreover, as illustrated in FIGS. 5 and 13, the heat exchange unit 14 and the gas exchange unit 16 are formed by cutting both end portions of the first cylindrical unit 94 and the second cylindrical unit 98 along the first cutting line C1 (see FIG. 12) and a second cutting line C2 (see FIG. 12) in the cutting step (step S6).

At this time, a part of each of the first cap member 92a, the first annular member 96a, the second cap member 92b, and the second annular member 96b is also cut off. In this manner, a part of the first cap member 92a is left between the heat exchange unit 14 and the first annular convex portion 42 and a part of the first annular member 96a is left between one end portions of the heat exchange unit 14 and the gas exchange unit 16. In addition, a part of the second cap member 92b is left between the heat exchange unit 14 and the second annular convex portion 52 and a part of the second annular member 96b is left between the other end portions of the heat exchange unit 14 and the gas exchange unit 16. Furthermore, the intermediate hollow fiber membrane 19 opens at the location of the first cutting line C1.

Moreover, in the sealing step (step S7), the outer sides of the first hollow fiber membrane 14a and the second hollow fiber membrane 16a at one end portions of the heat exchange unit 14 and the gas exchange unit 16 are sealed with the first sealing member 82a and the outer sides of the first hollow fiber membrane 14a and the second hollow fiber membrane 16a at the other end portions of the heat exchange unit 14 and the gas exchange unit 16 are sealed with the second sealing member 82b. At this time, the opening at the terminal end 19b of the intermediate hollow fiber membrane 19 is closed with the first sealing member 82a.

Figure 14:
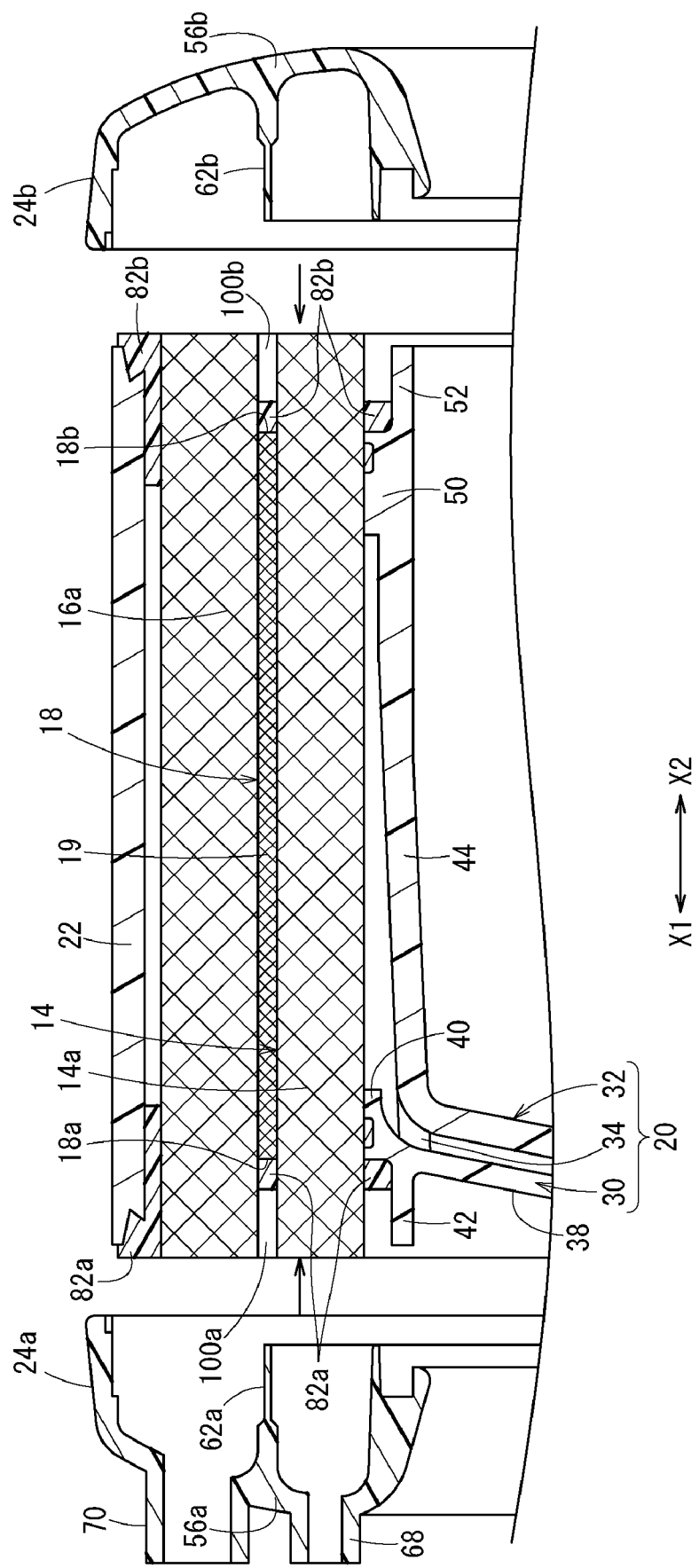
FIG. 14 is an explanatory view of a removal step and a mounting step.

Thereafter, as illustrated in FIGS. 5 and 14, the first cap member 92a, the first annular member 96a, the second cap member 92b, and the second annular member 96b are removed in the removal step (step S8). In this manner, a first gap 100a is formed between one end portions of the heat exchange unit 14 and the gas exchange unit 16 and a second gap 100b is formed between the other end portions of the heat exchange unit 14 and the gas exchange unit 16.

Moreover, in the mounting step (step S9), the first cover member 24a is fixed with the adhesive 64a in the state of being mounted on one end portions of the outer cylinder 22 and the core 20 and the second cover member 24b is fixed with the adhesive 64b in the state of being mounted on the other end portions of the outer cylinder 22 and the core 20. At this time, the protruding end portion of the first partition section 62a is inserted into the first gap 100a and the protruding end portion of the second partition section 62b is inserted into the second gap 100b. In this manner, the oxygenator 10 illustrated in FIG. 1 is manufactured.

Next, the effects of the present embodiment will be described below.

As illustrated in FIGS. 1 and 2, in the oxygenator 10, the first partition section 62a is inserted between one end portions of the heat exchange unit 14 and the gas exchange unit 16. The second partition section 62b is inserted between the other end portions of the heat exchange unit 14 and the gas exchange unit 16. The intermediate spacer 18 formed in a cylindrical shape is arranged between the heat exchange unit 14 and the gas exchange unit 16. The first end portion 18a of the intermediate spacer 18 is located at the part which does not overlap the first partition section 62a in the radial direction in one end portions of the heat exchange unit 14 and the gas exchange unit 16.

In this manner, it is possible to form the first gap 100a, into which the first partition section 62a can be inserted, between one end portions of the heat exchange unit 14 and the gas exchange unit 16 by the intermediate spacer 18. Hence, one end portion of the heat exchange unit 14 and one end portion of the gas exchange unit 16 are pushed (i.e., supported) in the radial direction by the first partition section 62a and it is possible to suppress the lumen of the first hollow fiber membrane 14a and the lumen of the second hollow fiber membrane 16a from being collapsed. Consequently, it is possible to suppress decreases in the heat exchange rate and the gas exchange rate.

The second end portion 18b of the intermediate spacer 18 is located at the part which does not overlap the second partition section 62b in the radial direction in the other end portions of the heat exchange unit 14 and the gas exchange unit 16. In this manner, it is possible to form the second gap 100b, into which the second partition section 62b can be inserted, between the other end portions of the heat exchange unit 14 and the gas exchange unit 16 by the intermediate spacer 18. Hence, the other end portion of the heat exchange unit 14 and the other end portion of the gas exchange unit 16 are pushed (i.e., supported) in the radial direction by the second partition section 62b and it is possible to suppress the lumen of the first hollow fiber membrane 14a and the lumen of the second hollow fiber membrane 16a from being collapsed. Consequently, it is possible to further suppress decreases in the heat exchange rate and the gas exchange rate.

The radial thickness of the part inserted between the end portions of the heat exchange unit 14 and the gas exchange unit 16 (thickness of the protruding end portion) of each of the first partition section 62a and the second partition section 62b is thinner than the wall thickness of the intermediate spacer 18. In this manner, it is possible to further suppress the lumen of the first hollow fiber membrane 14a and the lumen of the second hollow fiber membrane 16a from being collapsed by the first partition section 62a and the second partition section 62b.

The intermediate spacer 18 is formed so that fluid does not flow through the lumen of the intermediate hollow fiber membrane 19. In this manner, it is possible to avoid a decrease in the heat exchange rate or the gas exchange rate due to the gas (oxygen) and heat medium flowing through the lumen of the intermediate hollow fiber membrane 19.

The intermediate spacer 18 is comprised of one continuous intermediate hollow fiber membrane 19, and the opening at least at one end portion of the intermediate hollow fiber membrane 19 is closed. In this manner, it is possible to prevent the heat medium or gas from flowing through the lumen of the intermediate hollow fiber membrane 19 of the intermediate spacer 18.

The intermediate spacer 18 is formed as the intermediate hollow fiber membranes 19 overlap each other in the radial direction. In this manner, it is possible to easily adjust the radial thickness (wall thickness) of the intermediate spacer 18.

In the method for manufacturing the oxygenator 10, the intermediate spacer 18 is arranged on the outer surface of the first cylindrical unit 94 so that the first gap 100*a* is formed between one end portions of the heat exchange unit 14 and the gas exchange unit 16 and the second gap 100*b* is formed between the other end portions of the heat exchange unit 14 and the gas exchange unit 16 between the sealing step and the mounting step in the arrangement step. Moreover, in the mounting step, the first partition section 62*a* is inserted into the first gap 100*a* and the second partition section 62*b* is inserted into the second gap 100*b*. In this manner, it is possible to avoid decreases in the heat exchange rate and the gas exchange rate of the oxygenator 10.

In the arrangement step, the first annular member 96*a* is disposed so as to cover only one end portion of the first cylindrical unit 94 and the second annular member 96*b* is disposed so as to cover only the other end portion of the first cylindrical unit 94. In the second winding step, the second hollow fiber membrane 16*a* is wound around the outer surface of each of the intermediate spacer 18, the first annular member 96*a*, and the second annular member 96*b*. Moreover, the removal step of removing the first annular member 96*a* and the second annular member 96*b* is performed after the sealing step.

In this manner, it is possible to reliably form the first gap 100*a*, into which the protruding end of the first partition section 62*a* can be inserted, between one end portions of the heat exchange unit 14 and the gas exchange unit 16 by the first annular member 96*a*. In addition, it is possible to reliably form the second gap 100*b*, into which the protruding end of the second partition section 62*b* can be inserted, between the other end portions of the heat exchange unit 14 and the gas exchange unit 16 by the second annular member 96*b*.

In the first winding step, the first cylindrical unit 94 is formed by winding one continuous first hollow fiber membrane 14*a* and reciprocating the first hollow fiber membrane 14*a* plural times in the axial direction. In this manner, it is possible to efficiently form the first cylindrical unit 94. In the second winding step, the second cylindrical unit 98 is formed by winding one continuous second hollow fiber membrane 16*a* and reciprocating the second hollow fiber membrane 16*a* plural times in the axial direction. In this manner, it is possible to efficiently form the second cylindrical unit 98.

In the sealing step, the opening of the terminal end 19*b* of the intermediate hollow fiber membrane 19 constituting the intermediate spacer 18 is closed with the first sealing member 82*a*. In this manner, it is possible to prevent the fluid from flowing through the lumen of the intermediate hollow fiber membrane 19.

Figure 15:
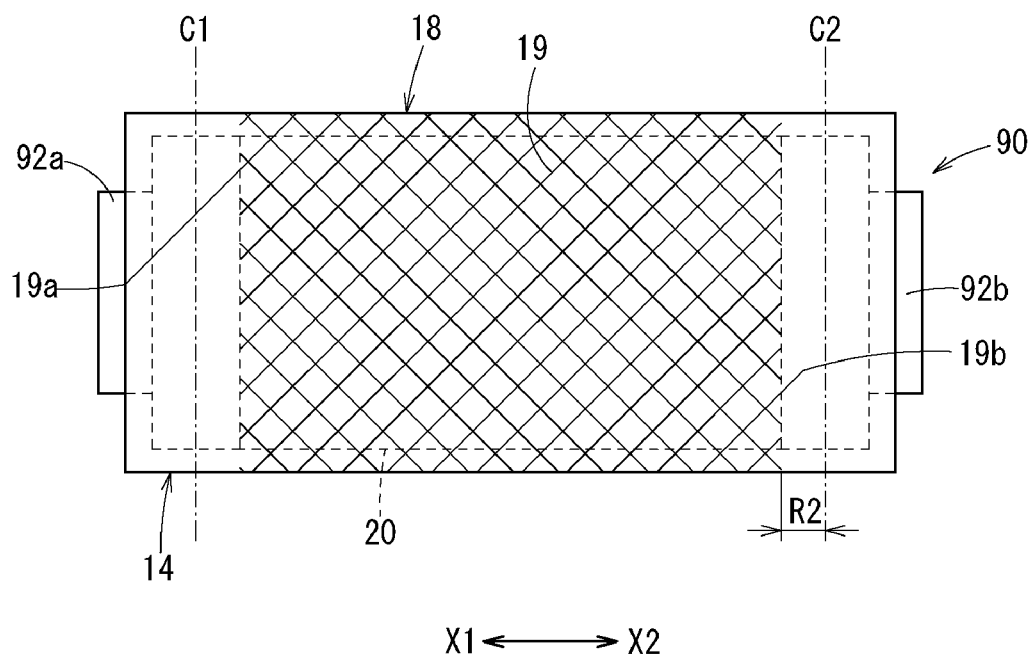
FIG. 15 is an explanatory view of a modification of an arrangement step.

As illustrated in FIG. 15, in the arrangement step, the intermediate hollow fiber membrane 19 may be cut so that the terminal end 19*b* thereof is located in a range R2 in which the second sealing member 82*b* is added of the first cylindrical unit 94. In other words, the terminal end 19*b* of the intermediate hollow fiber membrane 19 is located on the inner side (the first cap member 92*a* side) of the second cutting line C2. Moreover, the terminal end 19*b* of the intermediate hollow fiber membrane 19 is temporarily fixed to the first cylindrical unit 94. At this point in time, the terminal end 19*b* of the intermediate hollow fiber membrane 19 is open. In this case, the opening of the terminal end 19*b* of the intermediate hollow fiber membrane 19 is closed with the second sealing member 82*b* in the sealing step. A similar effect is exerted even in a case in which the intermediate spacer 18 is formed as described above.

In the oxygenator 10, the first end portion 18*a* of the intermediate spacer 18 may be located at a region which does not overlap the first partition section 62*a* in the radial direction in one end portions of the heat exchange unit 14 and the gas exchange unit 16 and the second end portion 18*b* may be located at a region (for example, the central portion in the axial direction) which is not the other end portions of the heat exchange unit 14 and the gas exchange unit 16. Even in this case, it is possible to suppress the lumen of the first hollow fiber membrane 14*a* and the lumen of the second hollow fiber membrane 16*a* from being collapsed by the first partition section 62*a* at one end portions of the heat exchange unit 14 and the gas exchange unit 16.

In some embodiments of the oxygenator 10, the heat exchange unit 14 may be located radially inward from the gas exchange unit 16.

In addition, in the oxygenator 10, the first end portion 18*a* of the intermediate spacer 18 may be located at a region (for example, the central portion in the axial direction) which is not one end portions of the heat exchange unit 14 and the gas exchange unit 16 and the second end portion 18*b* may be located at a region which does not overlap the second partition section 62*b* in the radial direction in the other end portions of the heat exchange unit 14 and the gas exchange unit 16.

In some embodiments of the method for manufacturing the oxygenator 10, the first annular member 96*a* and the second annular member 96*b* may not be provided on the outer surface of the first cylindrical unit 94 in the arrangement step. Even in this case, it is possible to form the first gap 100*a* and the second gap 100*b* by the intermediate spacer 18.

The oxygenator and the method for manufacturing the same according to the present invention are not limited to the above-described embodiments and may employ various configurations without departing from the gist of the present invention.

What is claimed is:

1. An oxygenator comprising:
a housing;
a cylindrical heat exchange unit comprised of a first hollow fiber membrane;
a cylindrical gas exchange unit comprised of a second hollow fiber membrane, wherein the first hollow fiber membrane and the second hollow fiber membrane are wound and are accommodated in the housing, wherein the heat exchange unit and the gas exchange unit overlap each other in a radial direction so that a blood flow path is formed on an outer side of the first hollow fiber membrane and an outer side of the second hollow fiber membrane, and wherein the housing includes a pair of partition sections that partition each of spaces on both sides in an axial direction from the heat exchange unit and the gas exchange unit into a heat medium flow path and a gas flow path; and
a cylindrical intermediate spacer arranged between the heat exchange unit and the gas exchange unit by winding an intermediate hollow fiber membrane, wherein at least one end portion of the intermediate spacer is located at a region that does not overlap the partition section in the radial direction in the end portions of the heat exchange unit and the gas exchange unit;

wherein the partition sections are each inserted in respective gaps between end portions of the heat exchange unit and the gas exchange unit, and wherein the partition sections are axially shifted from the intermediate spacer.

2. The oxygenator according to claim 1, wherein:
a radial thickness of a protruding end of the partition section inserted between the end portions of the heat exchange unit and the gas exchange unit is thinner than a radial wall thickness of the intermediate spacer.

3. The oxygenator according to claim 1, wherein:
the intermediate spacer is formed so that a fluid does not flow through a lumen of the intermediate hollow fiber membrane.

4. The oxygenator according to claim 3, wherein:
the intermediate spacer is comprised of one continuous intermediate hollow fiber membrane; and
an opening at least at one end portion of the intermediate hollow fiber membrane comprising the intermediate spacer is closed.

5. The oxygenator according to claim 1, wherein:
the intermediate spacer is formed such that the intermediate hollow fiber membranes overlap each other in the radial direction.

6. The oxygenator according to claim 1, wherein:
each end portion of the intermediate spacer is located at a region that does not overlap the partition section in the radial direction in the end portions of the heat exchange unit and the gas exchange unit.

7. A method for manufacturing an oxygenator including a heat exchange unit and a gas exchange unit that are disposed to overlap each other in a radial direction, the method comprising the steps of:
a first winding step of forming a first cylindrical unit by winding a first hollow fiber membrane on an outer surface of a core;
an arrangement step of arranging a cylindrical intermediate spacer by winding an intermediate hollow fiber membrane around an outer surface of the first cylindrical unit;
a second winding step of forming a second cylindrical unit by winding a second hollow fiber membrane around an outer surface of the intermediate spacer;
an outer cylinder disposition step of disposing an outer cylinder so as to cover an outer surface of the second cylindrical unit;
a cutting step of forming the heat exchange unit and the gas exchange unit by cutting both axial end portions of the first cylindrical unit and the second cylindrical unit;
a sealing step of sealing outer sides of the first hollow fiber membrane and the second hollow fiber membrane at both end portions of the heat exchange unit and the gas exchange unit with a sealing member; and a mounting step of mounting cover members on both end portions of the core and the outer cylinder and forming a heat medium flow path and a gas flow path in the respective cover members;

wherein the intermediate spacer is arranged on the outer surface of the first cylindrical unit so that a gap is formed at least between one end portions of the heat exchange unit and the gas exchange unit or between the other end portions of the heat exchange unit and the gas exchange unit when performing the mounting step in the arrangement step; and wherein a partition section of the cover member is inserted into the gap formed by the intermediate spacer in the mounting step.

8. The method for manufacturing an oxygenator according to claim 7:
wherein the intermediate spacer is arranged on the outer surface of the first cylindrical unit so that the gap is formed between one end portions of the heat exchange unit and the gas exchange unit and between the other end portions of the heat exchange unit and the gas exchange unit when performing the mounting step in the arrangement step; and
wherein a protruding end of the partition section of each of the cover members is inserted into each of the gaps formed by the intermediate spacer in the mounting step.

9. The method for manufacturing an oxygenator according to claim 7:
wherein an annular member is disposed so as to cover only both end portions of the first cylindrical unit in the arrangement step;
wherein the second hollow fiber membrane is wound around an outer surface of each of the intermediate spacer and the annular member in the second winding step; and
wherein a removal step of removing the annular member is performed after the sealing step.

10. The method for manufacturing an oxygenator according to claim 7:
wherein the first cylindrical unit is formed by winding one continuous first hollow fiber membrane around the outer surface of the first cylindrical unit and reciprocating the one continuous first hollow fiber membrane a plurality of times in an axial direction in the first winding step; and
wherein the second cylindrical unit is formed by winding one continuous second hollow fiber membrane around the outer surface of the intermediate spacer and reciprocating the one continuous second hollow fiber membrane a plurality of times in the axial direction in the second winding step.

11. The method for manufacturing an oxygenator according to claim 7:
wherein an opening at least at one end portion of the intermediate hollow fiber membrane constituting the intermediate spacer is closed with the sealing member in the sealing step.

* * * * *